(12) United States Patent
Hagen et al.

(10) Patent No.: US 7,625,918 B2
(45) Date of Patent: Dec. 1, 2009

(54) HYDROCODONE POLYMORPHS

(75) Inventors: Eric J. Hagen, Lafayette, IN (US); Aeri Park, West Lafayette, IN (US)

(73) Assignee: Noramco, Inc., Athens, GA (US)

( * ) Notice: Subject to any disclaimer, the term of this patent is extended or adjusted under 35 U.S.C. 154(b) by 420 days.

(21) Appl. No.: 11/371,377

(22) Filed: Mar. 8, 2006

(65) Prior Publication Data

US 2007/0072889 A1    Mar. 29, 2007

Related U.S. Application Data

(60) Provisional application No. 60/693,209, filed on Jun. 23, 2005, provisional application No. 60/660,645, filed on Mar. 11, 2005.

(51) Int. Cl.
*A61K 31/485* (2006.01)
*C07D 489/02* (2006.01)

(52) U.S. Cl. .......................... 514/282; 546/45; 546/44

(58) Field of Classification Search ................ 514/282; 546/45, 44
See application file for complete search history.

(56) References Cited

U.S. PATENT DOCUMENTS 2,544,291 A    3/1951    Baizer 2,577,947 A    12/1951    Baizer et al.

FOREIGN PATENT DOCUMENTS

| EP | 0 900 582 A1 | 3/1999 |
|---|---|---|
| WO | WO 2005/100361 A1 | 10/2005 |
| WO | WO 2006/052456 A1 | 5/2006 |

OTHER PUBLICATIONS

Barnes et al, "Physical Methods for the Identification of Narcotics (Cont.) Part IIB. X-Ray Diffraction Powder Data for Eighty-Three Narcotics", *Bulletin on Narcotics* (1994) pp. 27-68 (XP009070139).
Parfitt, "Hydrocodone Tartrate", *Martindale: The Complete Drug Reference* (formerly Martindale the Extra Pharmacopoeia), London, Pharmaceutical Press, GB (1999) p. 43, ISBN: 0-85369-429-X (XP002394987).
Budavari et al, "4806. Hydrocodone", *Merck Index. Encyclopedia of Chemicals, Drugs, and Biologicals 13th Edition 2001*, Whitehouse Station, Merck & Co., US, vol. Ed. 13 (2001) pp. 854-855, ISBN: 0-911910-12-3 (XP002394988).
Caira, "Crystalline Polymorphism of Organic Compounds", *Topics in Current Chemistry*, Springer, Berlin, DE, vol. 198 (1998) pp. 163-208, ISSN: 0340-1022 (XP001156954).
Britain et al, "Polymorphism in Pharmaceutical Solids Passage", *Polymorphism in Pharmaceutical Solids* (1999) pp. 235-238 (XP002278123).

*Primary Examiner*—Charanjit S Aulakh

(57) ABSTRACT

Hydrocodone bitartrate forms are disclosed which are useful as analgesic agents either in combination with or as replacements for hydrocodone bitartrate.

30 Claims, 11 Drawing Sheets

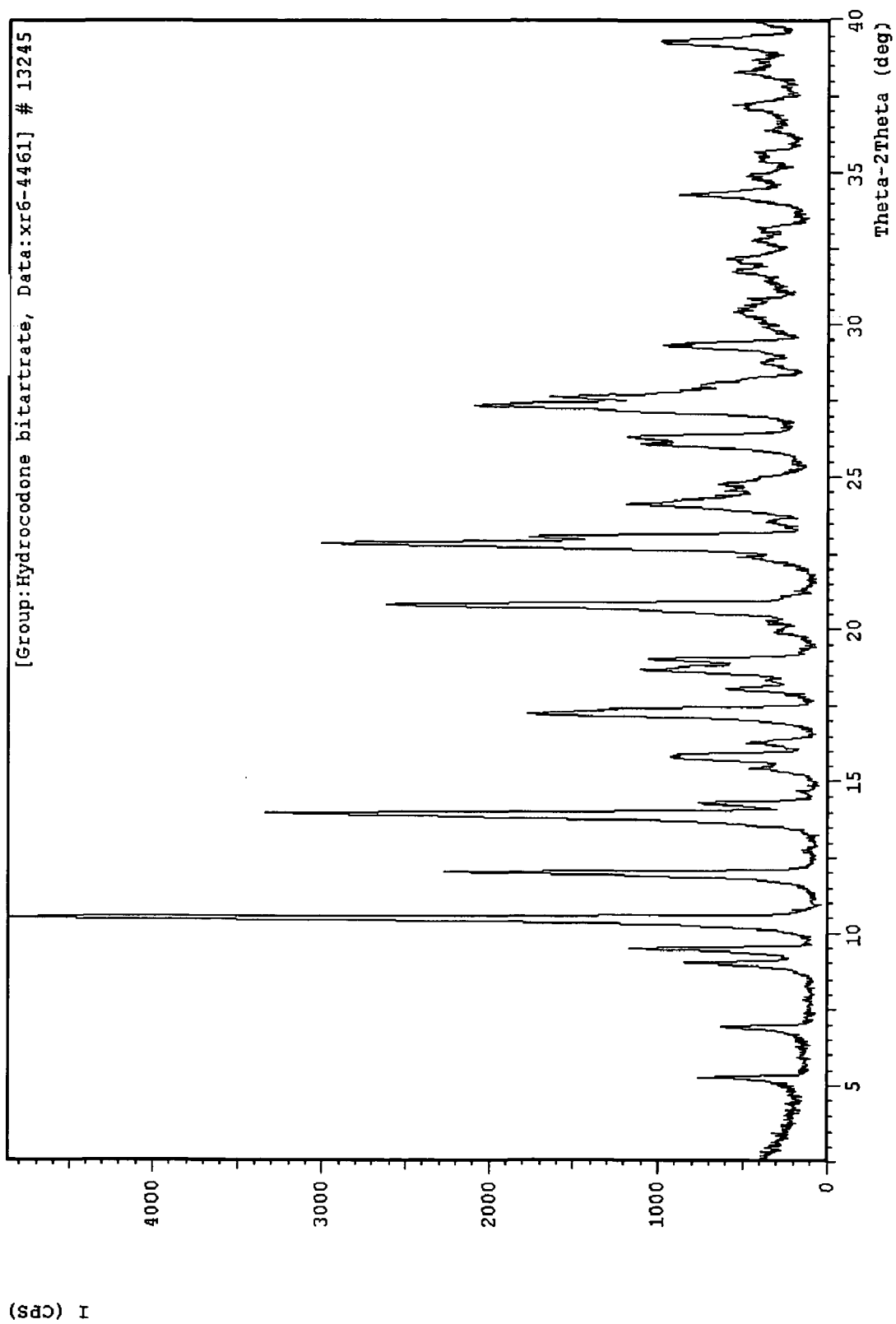
Figure 1 XRPD of Form I

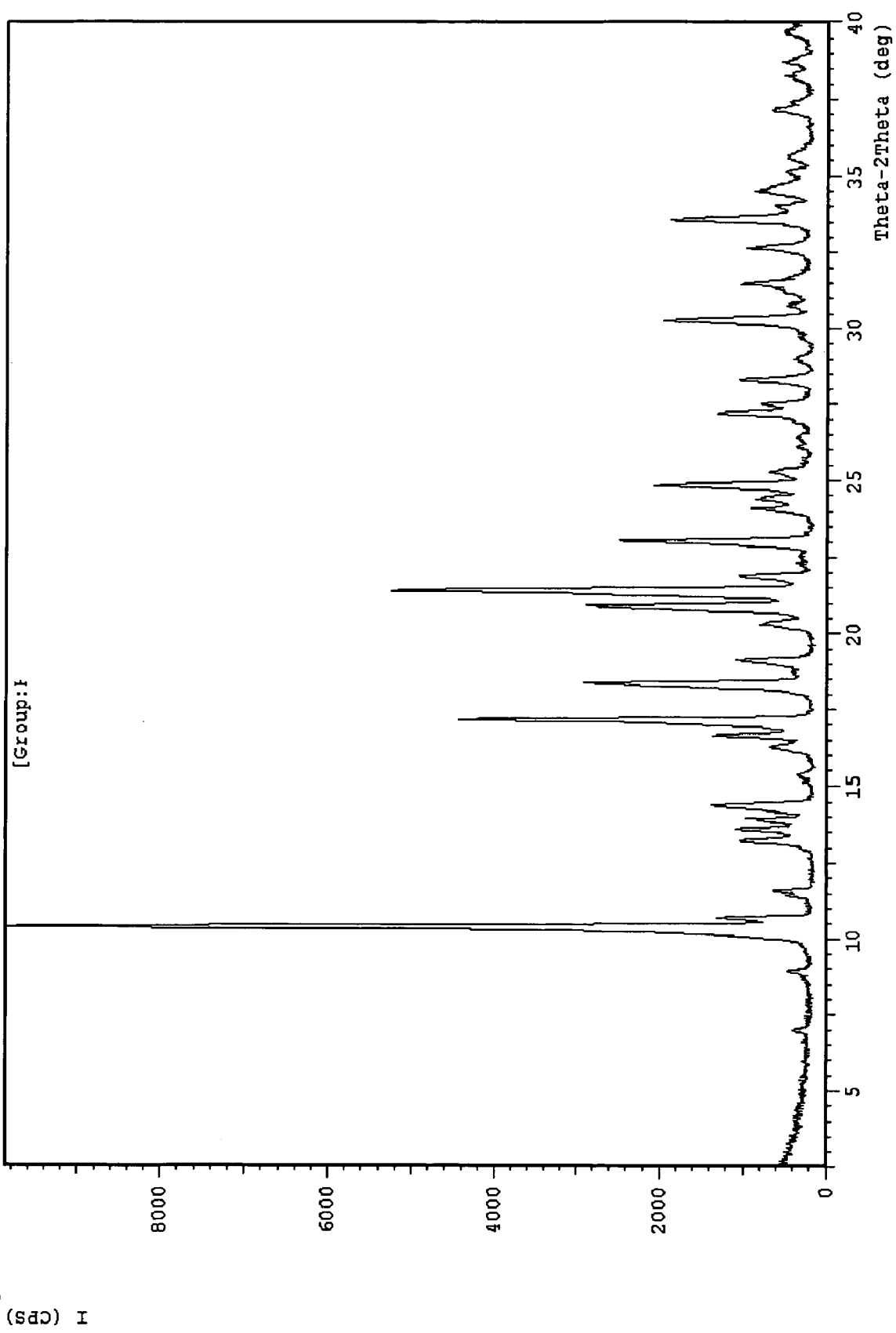
Figure 2 XRPD of Form II

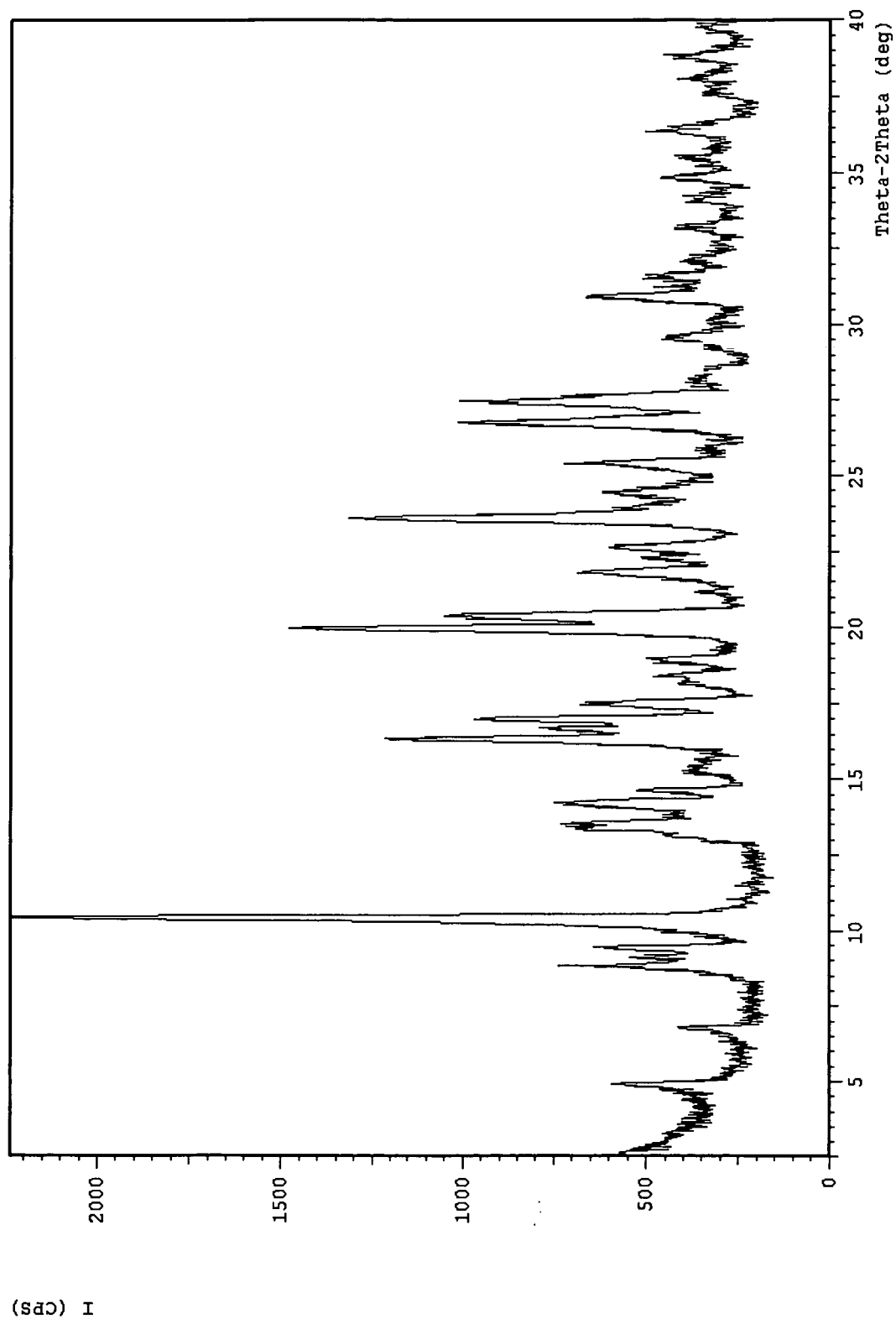
Figure 3 XRPD of Form III

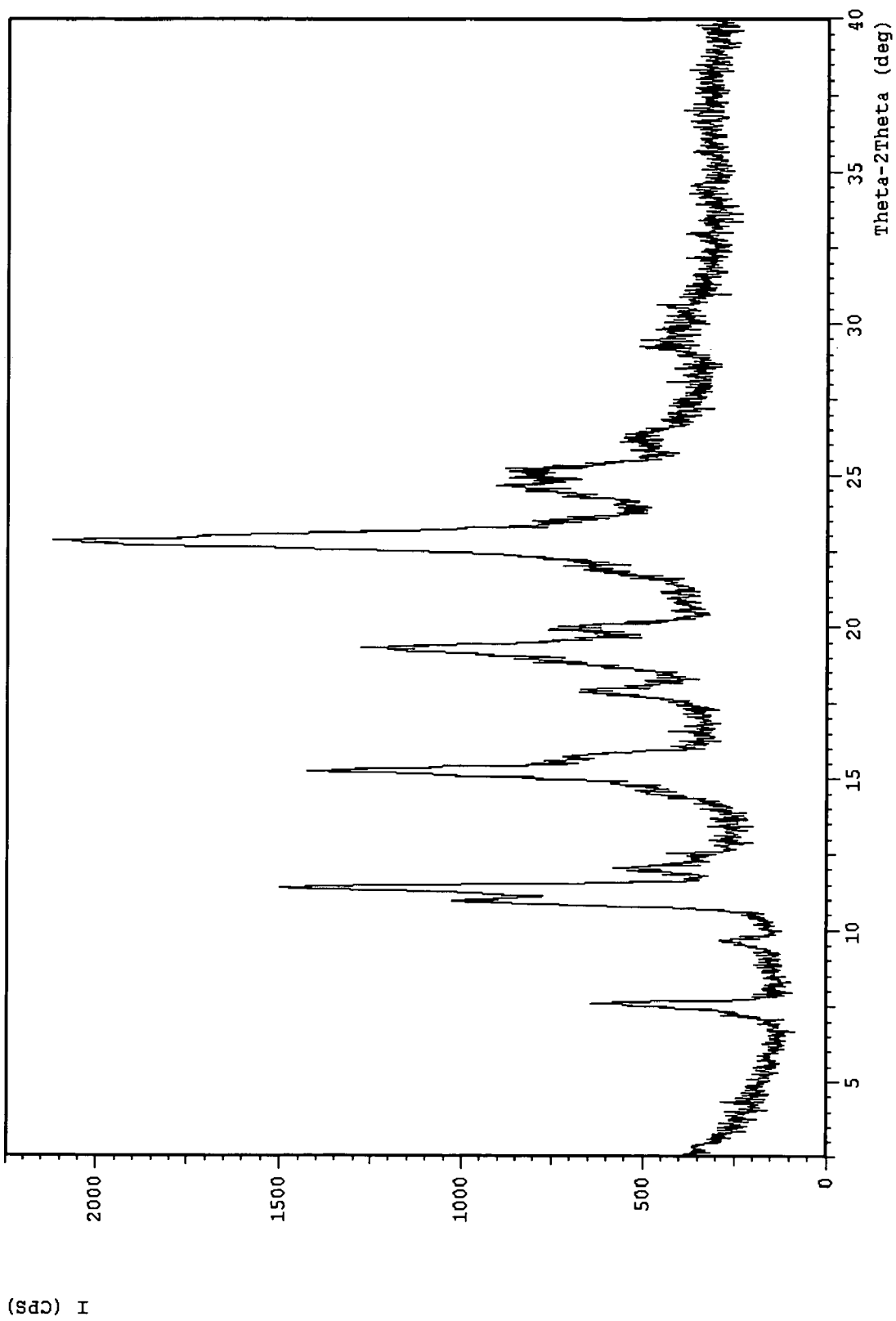
Figure 4 XRPD of Form IV

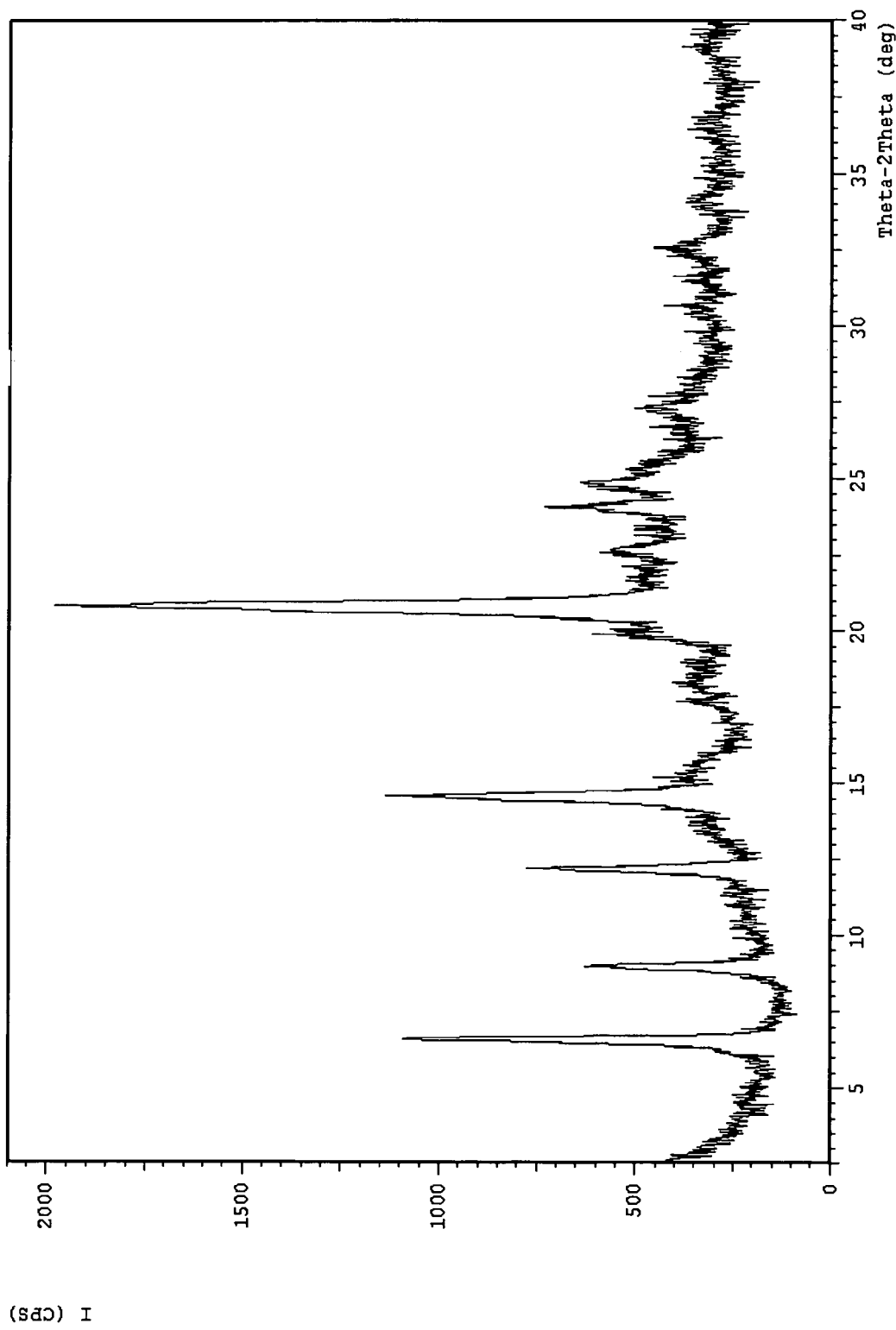
Figure 5 XRPD of Form V

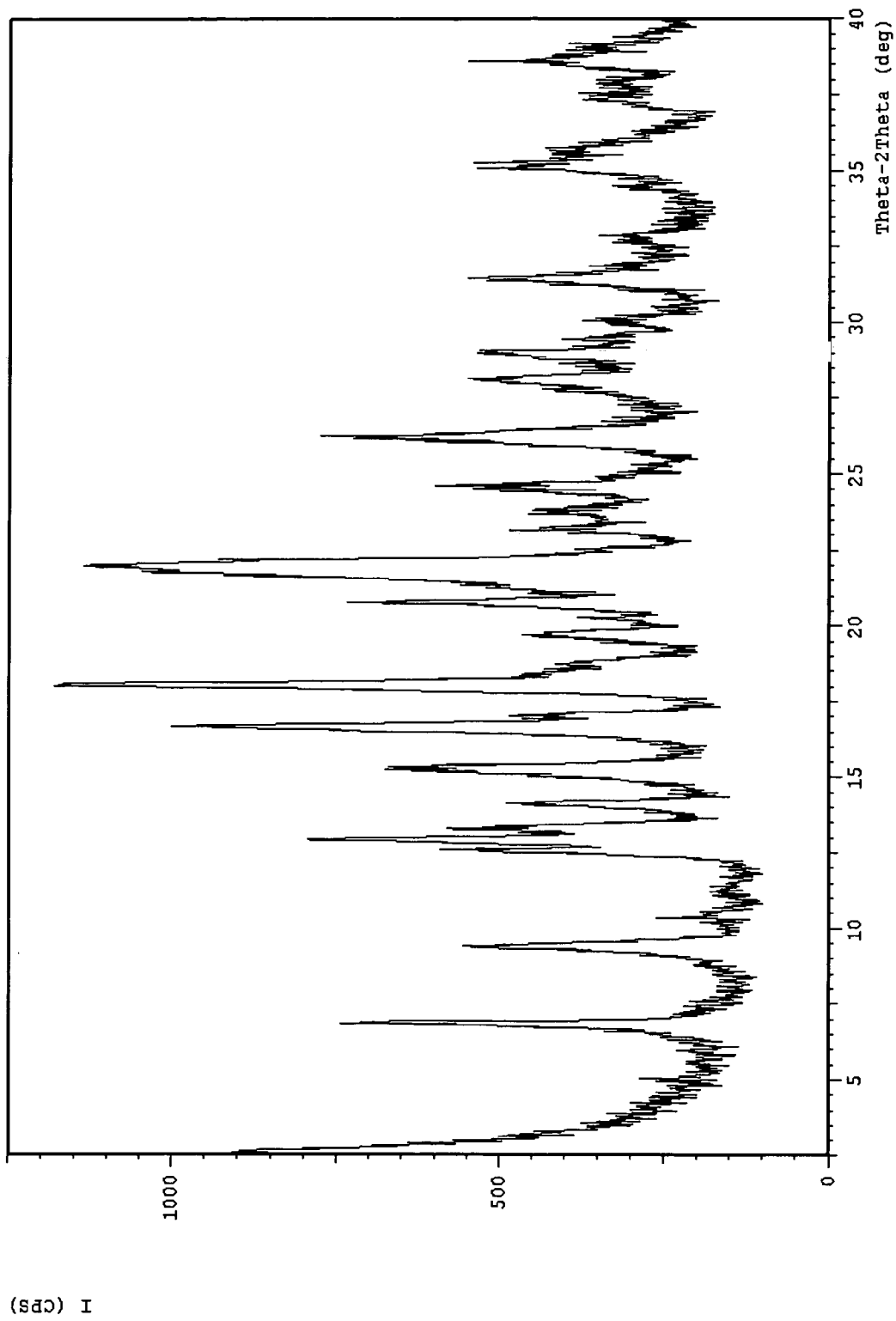
Figure 6 XRPD of Form VI

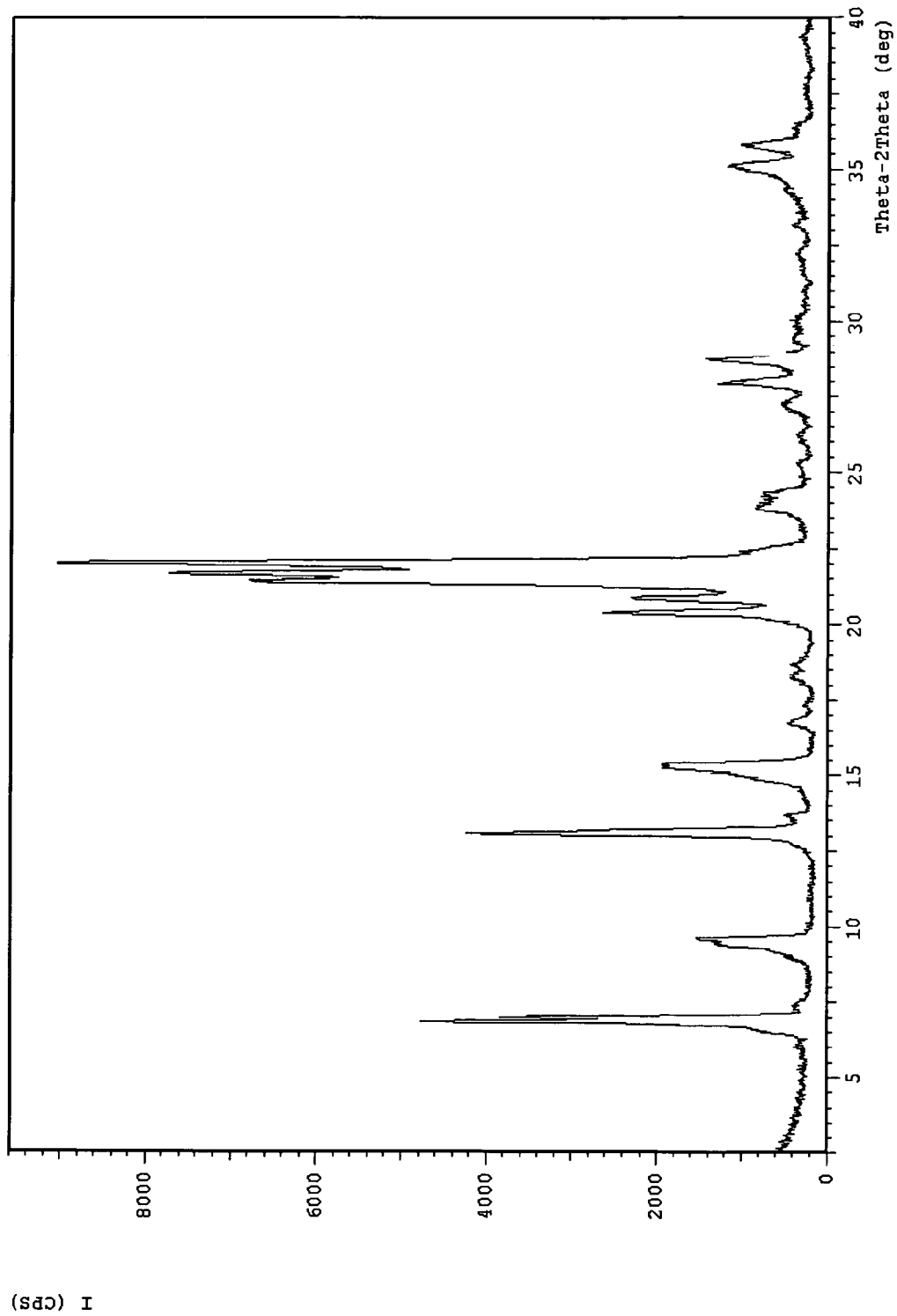
Figure 7 XRPD of Form VII

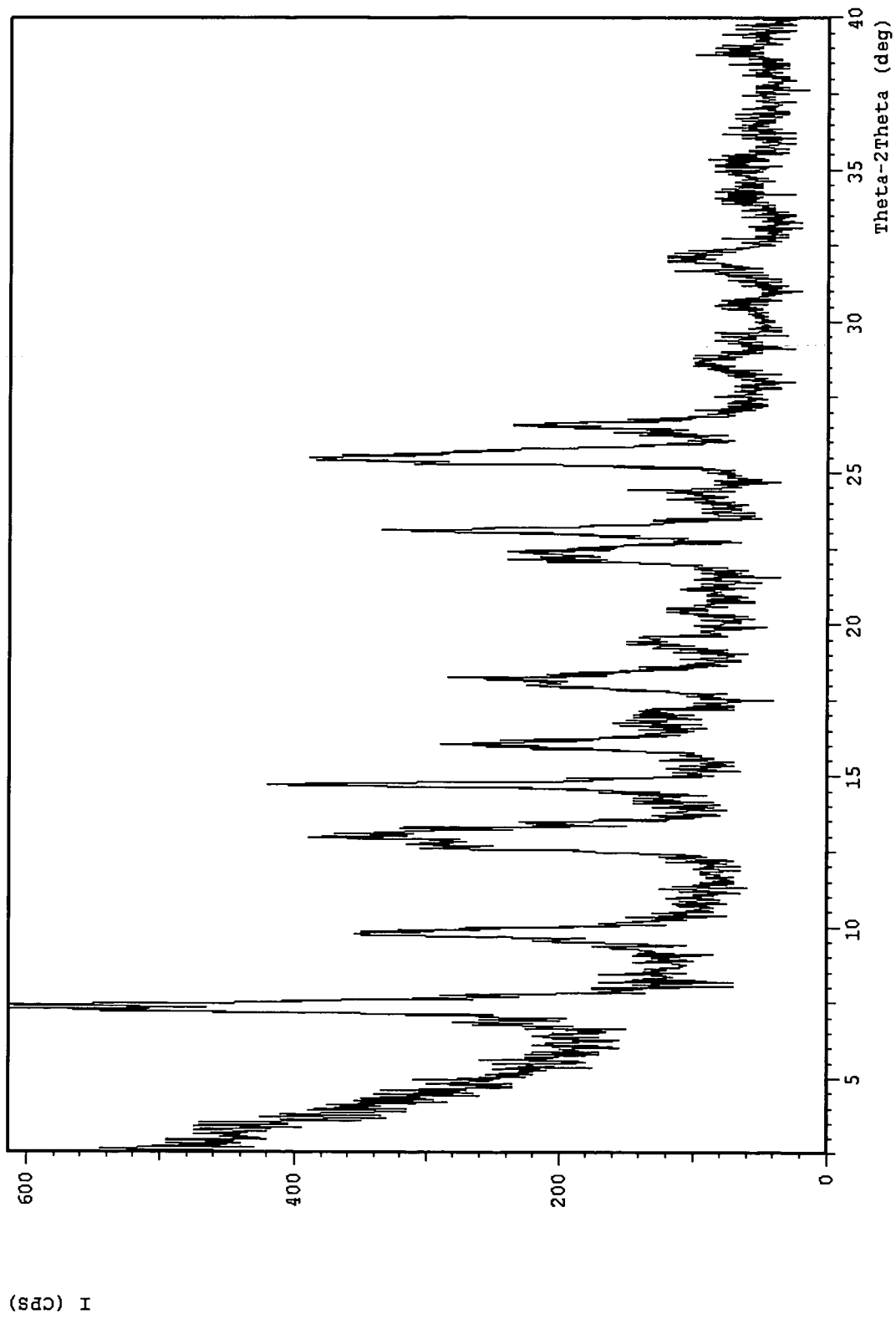
Figure 8 XRPD of Form VIII

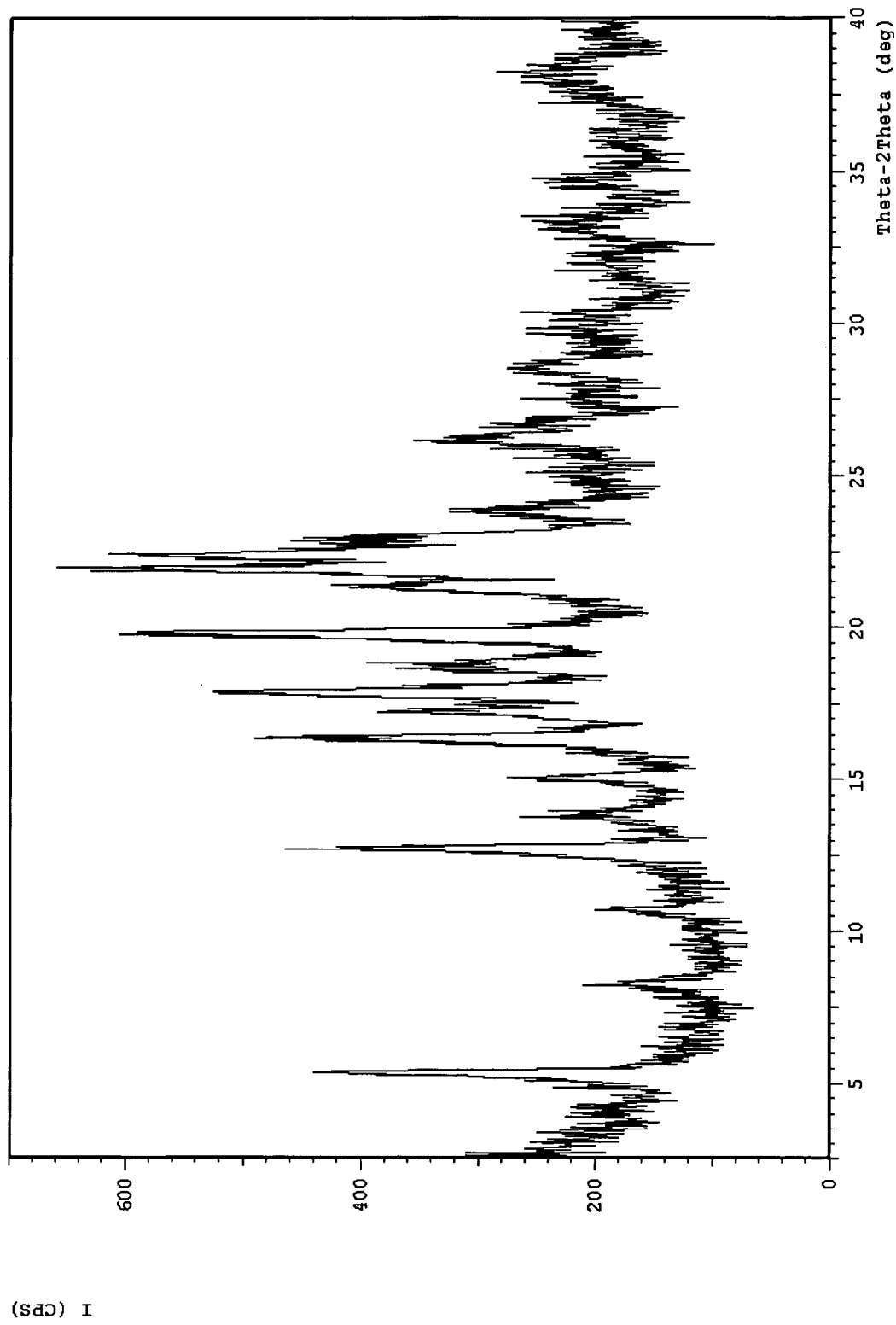
Figure 9 XRPD of Form IX

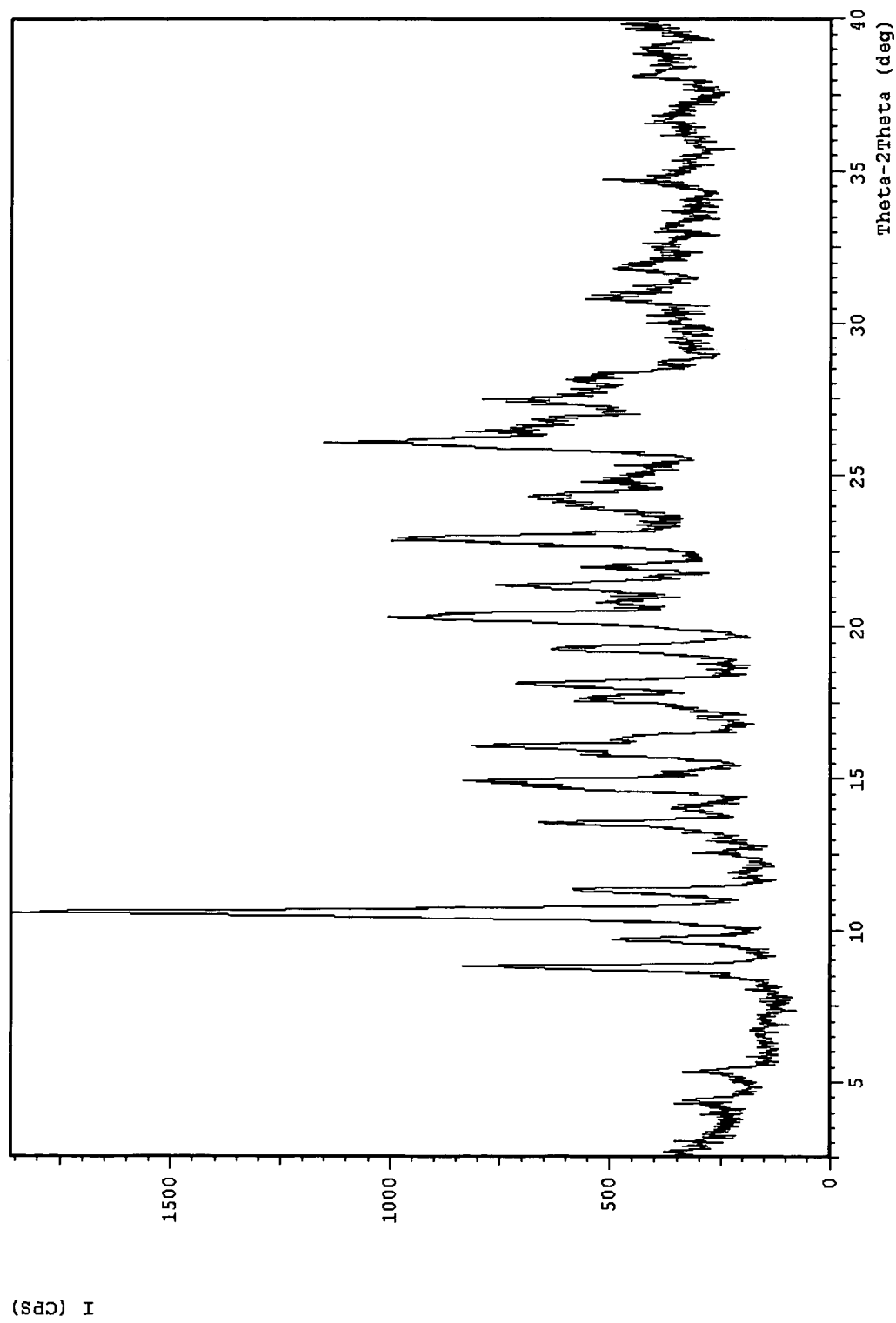
Figure 10 XRPD of Form X

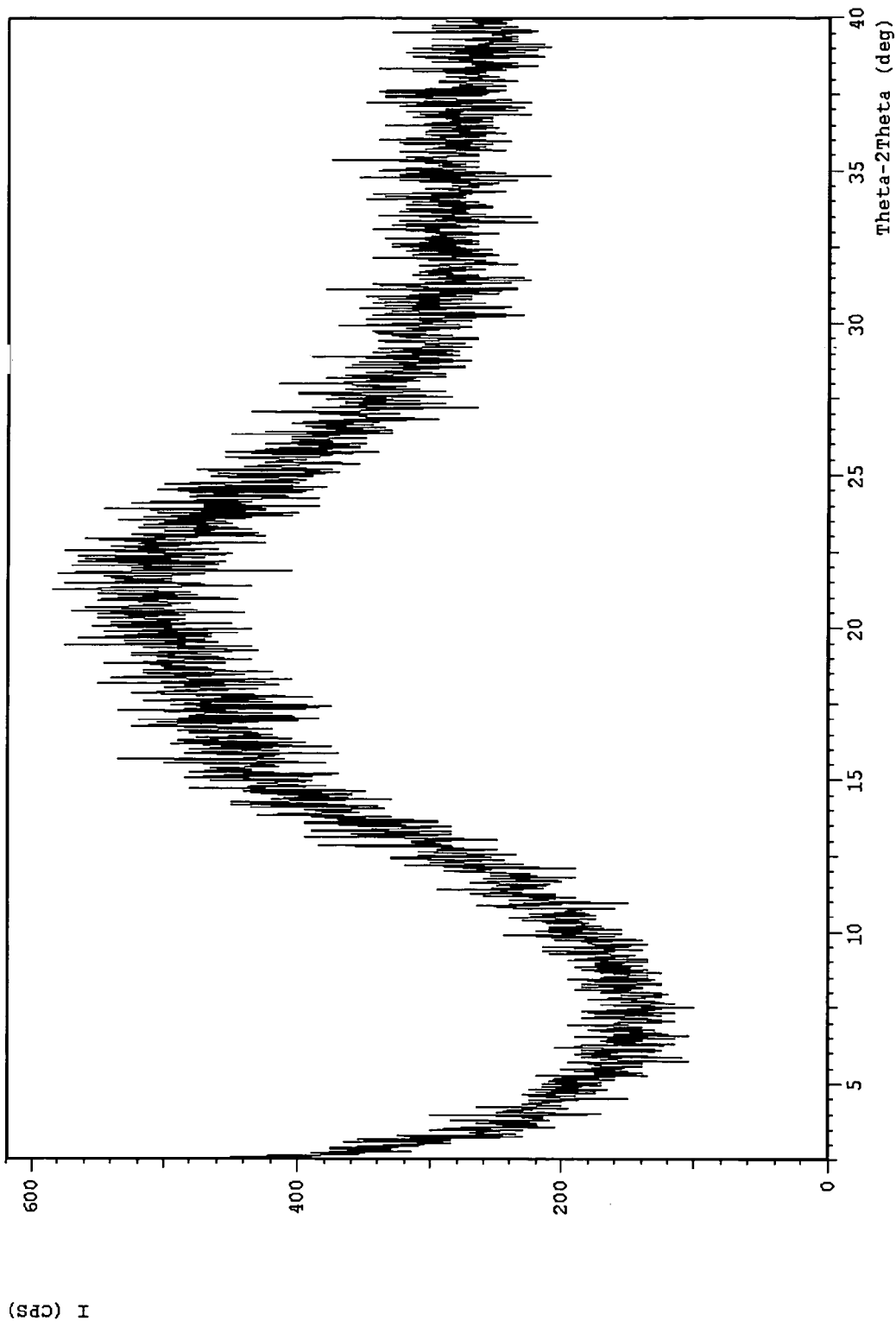
Figure 11 XRPD of Amorphous Hydrocodone Bitartrate

HYDROCODONE POLYMORPHS

CROSS REFERENCE TO RELATED APPLICATIONS

This application claims benefit to U.S. provisional application 60/660,645 filed on Mar. 11, 2005, and also to U.S. provisional application 60/693,209, filed on Jun. 23, 2005.

BACKGROUND OF THE INVENTION

Hydrocodone (4,5a-epoxy-3-methoxy-17-methylmorphinan-6-one tartrate (1:1) hydrate (2:5), dihydrocodeinone) is a semi synthetic opioid structurally related to codeine and is approximately equipotent to morphine in producing opiate-like effects. It is also known as hydrocodone bitartrate. Hydrocodone bitartrate is well known as an antitussive agent and an effective analgesic for mild to moderate pain control. In its most usual product forms hydrocodone bitartrate is combined with acetaminophen, aspirin, ibuprofen, and antihistamines. It is commercially available in tablet, capsule, and liquid forms. Hydrocodone bitartrate is available as Vicodin®, Lortab®, Vicoprofen®, Tussionex®, Hycomine®, and many other products. The drug is most often administered orally, typically in dosage forms of 5, 7.5, and 10 mg.

SUMMARY OF THE INVENTION

The present invention is directed to ten novel forms of hydrocodone bitartrate. These are identified herein as Forms II-X and an amorphous form. The known form of hydrocodone bitartrate is referred to hereinafter as hydrocodone bitartrate Form I.

DETAILED DESCRIPTION

All ten forms are derived directly or indirectly from hydrocodone bitartrate (hydrocodone bitartrate Form I) and are characterized by physical data, most notable by their X-ray powder diffraction XRPD patterns expressed in terms of °2θ and the relative intensities of the X-ray diffraction peaks.

One aspect of the invention is the novel forms of hydrocodone bitartrate. Another aspect of this invention is processes to make these novel forms. These novel forms of hydrocodone bitartrate can be used instead of or in combination with hydrocodone bitartrate for its pharmacological effects. The novel forms may be produced and used as the pure form, or the forms may be produced and used in combination with the other novel forms and/or hydrocodone bitartrate Form I. Another aspect of the invention is compositions comprising therapeutically effective amounts of one or more of these novel forms, optionally in combination with hydrocodone bitartrate Form I, and pharmaceutically acceptable carriers therefor. Another aspect is a method of providing a therapeutic (e.g., analgesic) effect to a mammal, preferably a human, in need thereof which comprises administering to said mammal a therapeutic amount of one or more of a novel form of the invention, optionally in combination with hydrocodone bitartrate. Hydrocodone bitartrate, its therapeutic uses and dose ranges, modes of administration, etc. are all well known in the art.

By pure is meant that each form of the invention is about 90-100%, preferably 95-100%, more preferably 98-100% (wt./wt.) pure; e.g. free of other hydrocodone bitartrate forms, solvents, and/or other undesirable non-hydrocodone bitartrate impurities. A preferred form of the invention is one that is free of other hydrocodone bitartrate forms, preferably 98-100% free.

One embodiment of the invention is the forms of hydrocodone bitartrate made by the processes such as recited in the examples. Another embodiment of the invention is the forms of hydrocodone bitartrate as identified by the X-ray powder diffraction patterns shown below.

BRIEF DESCRIPTION OF THE DRAWINGS

FIG. 1 is an X-ray powder diffraction pattern of hydrocodone bitartrate Form I expressed in terms of °2θ.

FIG. 2 is an X-ray powder diffraction pattern of hydrocodone bitartrate Form II expressed in terms of °2θ.

FIG. 3 is an X-ray powder diffraction pattern of hydrocodone bitartrate Form III expressed in terms of °2θ.

FIG. 4 is an X-ray powder diffraction pattern of hydrocodone bitartrate Form IV expressed in terms of °2θ.

FIG. 5 is an X-ray powder diffraction pattern of hydrocodone bitartrate Form V expressed in terms of °2θ.

FIG. 6 is an X-ray powder diffraction pattern of hydrocodone bitartrate Form VI expressed in terms of °2θ.

FIG. 7 is an X-ray powder diffraction pattern of hydrocodone bitartrate Form VII expressed in terms of °2θ.

FIG. 8 is an X-ray powder diffraction pattern of hydrocodone bitartrate Form VIII expressed in terms of °2θ.

FIG. 9 is an X-ray powder diffraction pattern of hydrocodone bitartrate Form IX expressed in terms of °2θ.

FIG. 10 is an X-ray powder diffraction pattern of hydrocodone bitartrate Form X expressed in terms of °2θ.

FIG. 11 is an X-ray powder diffraction pattern of hydrocodone bitartrate, amorphous form expressed in terms of °2θ.

Tables I and II summarize the prominent peaks of the X-ray powder diffraction patterns of each hydrocodone bitartrate form. The relative intensity (R.I.) (I/Io≧10) of each peak is shown, wherein R.I. is the ratio of the height of each peak compared to the highest peak, which is designated as 100%.

The data were generated using a Shimadzu v 4.1 X-ray powder diffractometer using Cu Kα radiation, fitted with a fine-focus X-ray tube, set at 40 kV and 40 mA. The divergence and scattering slits were set at 1° and the receiving slit was set at 0.15 mm. Diffracted radiation was detected by a NaI scintillation detector. A theta-two theta continuous scan was used at 3°/min (0.4 sec/0.02° step) from 2.5 to 40 °2θ.

TABLES I & II

Hydrocodone XRPD °2θ Peaks and Relative Intensities

TABLE I

| Form I | | Form II | | Form III | | Form IV | | Form V | |
|---|---|---|---|---|---|---|---|---|---|
| °2θ | I/Io | °2θ | I/Io | °2θ | I/Io | °2θ | I/Io | °2θ | I/Io |
| 5.25 | 11 | 10.39 | 100 | 4.86 | 14 | 7.54 | 22 | 6.57 | 56 |
| 6.90 | 10 | 10.66 | 11 | 6.74 | 10 | 11.21 | 66 | 8.96 | 27 |

TABLE I-continued

| Form I | | Form II | | Form III | | Form IV | | Form V | |
|---|---|---|---|---|---|---|---|---|---|
| °2θ | I/Io | °2θ | I/Io | °2θ | I/Io | °2θ | I/Io | °2θ | I/Io |
| 9.01 | 15 | 14.36 | 12 | 8.82 | 21 | 12.09 | 16 | 12.16 | 30 |
| 9.48 | 21 | 16.61 | 12 | 9.10 | 13 | 15.24 | 57 | 14.54 | 53 |
| 10.22 | 13 | 16.98 | 14 | 9.40 | 19 | 15.66 | 24 | 15.16 | 10 |
| 10.48 | 100 | 17.13 | 43 | 10.40 | 100 | 17.87 | 16 | 19.88 | 14 |
| 11.98 | 45 | 18.32 | 28 | 13.44 | 22 | 19.21 | 49 | 20.76 | 100 |
| 13.89 | 67 | 20.86 | 27 | 14.16 | 23 | 19.98 | 19 | 22.62 | 12 |
| 14.26 | 14 | 21.22 | 17 | 14.61 | 12 | 21.74 | 11 | 24.04 | 17 |
| 15.80 | 17 | 21.37 | 53 | 16.30 | 45 | 22.80 | 100 | 24.82 | 15 |
| 17.22 | 35 | 23.01 | 25 | 16.64 | 24 | 23.54 | 18 | | |
| 17.38 | 24 | 24.81 | 19 | 16.96 | 35 | 24.58 | 26 | | |
| 18.68 | 20 | 27.17 | 12 | 17.48 | 19 | 25.02 | 27 | | |
| 18.99 | 21 | 28.29 | 10 | 18.91 | 10 | | | | |
| 20.52 | 11 | 30.24 | 19 | 19.94 | 60 | | | | |
| 20.78 | 54 | 33.55 | 20 | 20.33 | 40 | | | | |
| 22.80 | 62 | | | 21.78 | 20 | | | | |
| 23.06 | 36 | | | 22.24 | 10 | | | | |
| 24.12 | 22 | | | 22.60 | 16 | | | | |
| 24.26 | 13 | | | 23.57 | 51 | | | | |
| 26.06 | 19 | | | 23.96 | 12 | | | | |
| 26.32 | 21 | | | 24.41 | 14 | | | | |
| 27.30 | 39 | | | 25.38 | 18 | | | | |
| 27.58 | 29 | | | 26.74 | 35 | | | | |
| 28.02 | 12 | | | 27.42 | 34 | | | | |
| 29.31 | 16 | | | 27.68 | 17 | | | | |
| 34.26 | 15 | | | 29.51 | 10 | | | | |
| 39.26 | 17 | | | 30.87 | 19 | | | | |
| | | | | 31.54 | 10 | | | | |
| | | | | 36.40 | 11 | | | | |

TABLE II

| Form VI | | Form VII | | Form VIII | | Form IX | | Form X | |
|---|---|---|---|---|---|---|---|---|---|
| °2θ | I/Io | °2θ | I/Io | °2θ | I/Io | °2θ | I/Io | °2θ | I/Io |
| 6.54 | 12 | 6.90 | 40 | 6.82 | 16 | 5.28 | 47 | 8.75 | 36 |
| 6.85 | 51 | 9.42 | 12 | 7.35 | 100 | 8.21 | 10 | 9.67 | 18 |
| 9.39 | 40 | 9.56 | 14 | 9.79 | 56 | 12.66 | 52 | 10.56 | 100 |
| 12.54 | 36 | 13.08 | 42 | 12.70 | 49 | 13.81 | 19 | 11.28 | 24 |
| 12.92 | 62 | 15.22 | 20 | 13.00 | 64 | 15.02 | 20 | 13.51 | 26 |
| 13.30 | 37 | 20.37 | 25 | 14.70 | 57 | 16.32 | 58 | 14.82 | 34 |
| 14.10 | 28 | 20.85 | 24 | 16.04 | 39 | 17.78 | 73 | 15.80 | 19 |
| 15.23 | 48 | 21.38 | 71 | 16.78 | 11 | 18.70 | 42 | 16.04 | 35 |
| 16.62 | 78 | 21.64 | 81 | 17.08 | 12 | 19.74 | 85 | 16.32 | 16 |
| 17.00 | 24 | 21.98 | 100 | 18.11 | 37 | 22.22 | 100 | 17.61 | 20 |
| 18.01 | 100 | 27.95 | 11 | 19.43 | 14 | 23.80 | 29 | 18.07 | 28 |
| 18.82 | 15 | 28.70 | 13 | 22.27 | 33 | 24.86 | 12 | 19.26 | 24 |
| 19.67 | 23 | 35.03 | 11 | 23.07 | 49 | 26.33 | 37 | 20.30 | 42 |
| 20.75 | 43 | | | 24.33 | 10 | 28.52 | 26 | 20.78 | 13 |
| 21.22 | 24 | | | 25.50 | 78 | 29.86 | 16 | 21.33 | 26 |
| 21.85 | 92 | | | 26.54 | 34 | 31.92 | 12 | 21.98 | 14 |
| 23.21 | 17 | | | 28.62 | 13 | 33.21 | 19 | 22.87 | 41 |
| 23.76 | 16 | | | 32.09 | 17 | 34.67 | 16 | 24.00 | 14 |
| 24.52 | 27 | | | | | 38.15 | 25 | 24.28 | 19 |
| 26.15 | 48 | | | | | 39.54 | 11 | 26.06 | 43 |
| 27.74 | 14 | | | | | | | 26.44 | 25 |
| 28.06 | 30 | | | | | | | 26.78 | 17 |
| 28.52 | 10 | | | | | | | 27.45 | 22 |
| 28.91 | 30 | | | | | | | 27.80 | 11 |
| 29.38 | 13 | | | | | | | 28.06 | 14 |
| 30.03 | 11 | | | | | | | 28.26 | 12 |
| 31.40 | 33 | | | | | | | 30.86 | 11 |
| 31.88 | 12 | | | | | | | 38.11 | 11 |
| 32.74 | 10 | | | | | | | | |
| 34.46 | 10 | | | | | | | | |
| 35.14 | 29 | | | | | | | | |
| 35.66 | 20 | | | | | | | | |
| 35.96 | 11 | | | | | | | | |
| 37.28 | 13 | | | | | | | | |
| 37.80 | 10 | | | | | | | | |
| 38.58 | 22 | | | | | | | | |
| 39.08 | 11 | | | | | | | | |

Table III summarizes the peaks of the X-ray powder diffraction patterns of each hydrocodone bitartrate form that are unique (peaks that are not shared with other forms within ±0.20 °2θ) and/or four additional intense peaks to make up a unique set for each form.

TABLE III

Crystalline Hydrocodone Bitartrate XRPD Unique Peaks

| Form I | Form II | Form III | Form IV | Form V | Form VI | Form VII | Form VIII | Form IX | Form X |
|---|---|---|---|---|---|---|---|---|---|
| 9.48 | 10.39* | 4.86 | 7.54 | 6.57 | 12.54 | 13.08 | 7.35* | 8.21 | 8.75 |
| 10.48* | 17.13 | 6.74 | 11.21 | 12.16 | 12.92 | 21.64 | 14.70 | 12.66 | 10.56* |
| 11.98 | 18.32 | 8.82 | 19.21 | 14.54 | 18.01* | 21.98* | 25.50 | 17.78 | 18.07 |
| 26.06 | 21.37 | 10.40* | 22.80* | 20.76* | 26.15 | 28.70 | 26.54 | 19.74 | 22.87 |
| — | 23.01 | 26.74 | 25.02 | — | 28.91 | — | — | 22.22* | — |
| — | 30.24 | 36.40 | — | — | 32.74 | — | — | — | — |
| — | 33.55 | — | — | — | — | — | — | — | — |

*Denotes the peak of greatest intensity for each form

Table IV summarizes the peaks of the X-ray powder diffraction patterns of the amorphous hydrocodone bitartrate form as generated by a Shimadzu v 4.1 X-ray powder diffractometer.

TABLE IV

Amorphous Hydrocodone Bitartrate XRPD Peak Ranges

| Peak No. | Amorphous form Range (°2θ) |
|---|---|
| 1 | 7.28-30.76 |

The forms of the invention may be further defined by other physical properties such as those in Table V.

TABLE V

Unique Properties of Hydrocodone Bitartrate Polymorphs

| Form | Unique Properties | Comments |
|---|---|---|
| I | DSC* (endotherms) | 74, 118° C. |
|  | Hot stage Melt | 116° C. |
|  | Water/Volatiles (content) | water (2.1 moles) |
| II | DSC (endotherms) | 101° C. |
|  | Hot stage Melt | 131° C. |
|  | Water/Volatiles (content) | water (1.8 moles) |
| III | DSC (endotherms) | 91, 99° C. |
|  | Hot stage Melt | 106° C. |
|  | Water/Volatiles (content) | water (3 moles) |
| IV | DSC (endotherms) | 91, 129° C. |
|  | Hot stage Melt | 129° C. |
|  | Water/Volatiles (content) | water (0.4 mole) |
| V | DSC (endotherms) | 69, 87° C. |
|  | Hot stage Melt | 81° C. |
|  | Water/Volatiles (content) | water (2 moles) |
| VI | DSC (endotherms) | 93, 100° C. |
|  | Hot stage Melt | 104° C. |
|  | Water/Volatiles (content) | water (2.3 moles) |
| VII | DSC (endotherms) | 103, 105° C. |
|  | Hot stage Melt | 96° C. |
|  | Water/Volatiles (content) | water (2.3 moles) |
| VIII | DSC (endotherms) | 109° C. |
|  | Water/Volatiles (content) | acetonitrile (1 mole) |
| Amorphous form | DSC | Glass Transition ($T_g$) onset at 101° C. |

* Differential scanning calorimetry

One of skill in the art will know how to determine "Hot stage Melt" temperature. Briefly, hot stage melt is determined by placing a sample of the compound on a glass microscope stage and slowly increasing the temperature of the stage until melting of the compound is observed.

As used herein the term "hydrocodone bitartrate" when used alone and without modifiers, refers to the known form or Form I of hydrocodone bitartrate.

The invention is further defined by reference to the following examples, which are intended to be illustrative and not limiting.

EXAMPLE 1

Preparation of Form II 755 mg of hydrocodone bitartrate was dissolved in 13 mL of a 9:1 (v/v) water:ethanol. 2 mL of the solution was filtered through a 0.2-μm nylon syringe filter, placed in a fume hood uncapped for evaporation to dryness to yield the title form.

EXAMPLE 2

Preparation of Form III 1000 mg of hydrocodone bitartrate was dissolved in 17 mL of water. ~2 mL of the solution was filtered through a 0.2 μm nylon syringe filter, 16 mL of acetone was added to the filtrate. The solution was placed in a refrigerator at ~4° C. for 4 days, then placed in a freezer (−20° C.) for 1 day. The solid formed was vacuum filtered to afford the title form.

EXAMPLE 3

Preparation of Form IV 1000 mg of hydrocodone bitartrate was dissolved in 17 mL of water. 2 mL of the solution was filtered through a 0.2 μm nylon syringe filter, placed in a fume hood uncapped for evaporation to dryness, and dried under vacuum for 4 days to yield the title form.

EXAMPLE 4

Preparation of Form V 338 mg of hydrocodone bitartrate was dissolved in 7.5 mL of water. The solution was filtered through a 0.2 μm nylon syringe filter, added acetone (72.5 mL) to the filtrate. The solution was covered and placed in a freezer (−20° C.) for 5 days. The title form was then collected through vacuum filtration.

EXAMPLE 5

Preparation of Form VI 80 mg of hydrocodone bitartrate was dissolved in 20 mL of tetrahydrofuran at 60° C. The solution was filtered while warm and allowed to cool slowly to room temperature. After several hours of cooling, the sample was placed in a refrigerator (4° C.) for 3 days, and a freezer (−20° C.) for 8 days. The solids formed were collected through vacuum filtration, and dried under vacuum to yield the title form.

EXAMPLE 6

Preparation of Form VII 81 mg of hydrocodone bitartrate was dissolved in 13 mL of methanol and filtered through a 0.2 μm nylon syringe filter, The solution was placed in a freezer (−20° C.) for 9 days the solids formed were removed by vacuum filtration. Seven (7) mL of cooled ethyl ether was added to the filtered solution, covered and placed back into the freezer (−20° C.) for 39 days. The solid formed was vacuum filtered to yield the title form.

EXAMPLE 7

Preparation of Form VIII 95 mg of hydrocodone bitartrate was dissolved in 20 mL of acetonitrile. 5 mL of the solution was filtered through a 0.2 μm nylon syringe filter, left loosely capped in a fume hood to dryness to yield the title form.

EXAMPLE 8

Preparation of Form IX 802 mg of hydrocodone bitartrate was dissolved in 200 mL of tetrahydrofuran at 60° C. Half the solution was poured into a pre-warmed beaker, which was then placed in a dry ice/acetone bath. The beaker was then covered and placed in a freezer (−20° C.) for 26 days. The solids formed were removed by vacuum filtration. The filtrate was left uncovered in a fume hood to dryness to yield the title form.

EXAMPLE 9

Preparation of Form X 104 mg of hydrocodone bitartrate was dissolved in 20 mL of acetonitrile. The solution was filtered through a 0.2 μm nylon syringe filter and covered with a foil lid containing 5 pinholes, and left in a fume hood to dryness to yield the title form.

EXAMPLE 10

Preparation of Amorphous Form 43 mg of hydrocodone bitartrate was dissolved in 10 mL of tetrahydrofuran and 2 mL water. Half the solution was filtered through a 0.2-micrometer nylon syringe filter and the solution was allowed to evaporate without a cover (completely evaporated after 1 day) to yield the title form.

What is claimed is:

1. A form of hydrocodone bitartrate which is selected from the group consisting of: Form II, Form III, Form IV, Form V, Form VI, Form VII, Form VIII, Form IX, Form X, and an amorphous form; wherein Form II has the following XRPD °2θ peaks and relative intensities (I/Io):

| °2θ | I/Io |
| --- | --- |
| 10.39 | 100 |
| 10.66 | 11 |
| 14.36 | 12 |
| 16.61 | 12 |
| 16.98 | 14 |
| 17.13 | 43 |
| 18.32 | 28 |
| 20.86 | 27 |
| 21.22 | 17 |
| 21.37 | 53 |
| 23.01 | 25 |
| 24.81 | 19 |
| 27.17 | 12 |
| 28.29 | 10 |
| 30.24 | 19 |
| 33.55 | 20 |

Form III has the following XRPD °2θ peaks and relative intensities:

| °2θ | I/Io |
| --- | --- |
| 4.86 | 14 |
| 6.74 | 10 |
| 8.82 | 21 |
| 9.10 | 13 |
| 9.40 | 19 |
| 10.40 | 100 |
| 13.44 | 22 |
| 14.16 | 23 |
| 14.61 | 12 |
| 16.30 | 45 |
| 16.64 | 24 |
| 16.96 | 35 |
| 17.48 | 19 |
| 18.91 | 10 |
| 19.94 | 60 |
| 20.33 | 40 |
| 21.78 | 20 |
| 22.24 | 10 |
| 22.60 | 16 |
| 23.57 | 51 |
| 23.96 | 12 |
| 24.41 | 14 |
| 25.38 | 18 |
| 26.74 | 35 |
| 27.42 | 34 |
| 27.68 | 17 |
| 29.51 | 10 |
| 30.87 | 19 |
| 31.54 | 10 |
| 36.40 | 11 |

Form IV has the following XRPD °2θ peaks and relative intensities:

| °2θ | I/Io |
| --- | --- |
| 7.54 | 22 |
| 11.21 | 66 |
| 12.09 | 16 |
| 15.24 | 57 |
| 15.66 | 24 |
| 17.87 | 16 |
| 19.21 | 49 |
| 19.98 | 19 |
| 21.74 | 11 |
| 22.80 | 100 |
| 23.54 | 18 |
| 24.58 | 26 |
| 25.02 | 27 |

Form V has the following XRPD °2θ peaks and relative intensities:

| °2θ | I/Io |
| --- | --- |
| 6.57 | 56 |
| 8.96 | 27 |
| 12.16 | 30 |
| 14.54 | 53 |
| 15.16 | 10 |
| 19.88 | 14 |
| 20.76 | 100 |
| 22.62 | 12 |
| 24.04 | 17 |
| 24.82 | 15 |

Form VI has the following XRPD °2θ peaks and relative intensities:

| °2θ | I/Io |
| --- | --- |
| 6.54 | 12 |
| 6.85 | 51 |
| 9.39 | 40 |
| 12.54 | 36 |
| 12.92 | 62 |
| 13.30 | 37 |
| 14.10 | 28 |
| 15.23 | 48 |
| 16.62 | 78 |
| 17.00 | 24 |
| 18.01 | 100 |
| 18.82 | 15 |
| 19.67 | 23 |
| 20.75 | 43 |
| 21.22 | 24 |
| 21.85 | 92 |
| 23.21 | 17 |
| 23.76 | 16 |
| 24.52 | 27 |
| 26.15 | 48 |
| 27.74 | 14 |

-continued

| °2θ | I/Io |
|---|---|
| 28.06 | 30 |
| 28.52 | 10 |
| 28.91 | 30 |
| 29.38 | 13 |
| 30.03 | 11 |
| 31.40 | 33 |
| 31.88 | 12 |
| 32.74 | 10 |
| 34.46 | 10 |
| 35.14 | 29 |
| 35.66 | 20 |
| 35.96 | 11 |
| 37.28 | 13 |
| 37.80 | 10 |
| 38.58 | 22 |
| 39.08 | 11 |

Form VII has the following XRPD °2θ peaks and relative intensities:

| °2θ | I/Io |
|---|---|
| 6.90 | 40 |
| 9.42 | 12 |
| 9.56 | 14 |
| 13.08 | 42 |
| 15.22 | 20 |
| 20.37 | 25 |
| 20.85 | 24 |
| 21.38 | 71 |
| 21.64 | 81 |
| 21.98 | 100 |
| 27.95 | 11 |
| 28.70 | 13 |
| 35.03 | 11 |

Form VIII has the following XRPD °2θ peaks and relative intensities:

| °2θ | I/Io |
|---|---|
| 6.82 | 16 |
| 7.35 | 100 |
| 9.79 | 56 |
| 12.70 | 49 |
| 13.00 | 64 |
| 14.70 | 57 |
| 16.04 | 39 |
| 16.78 | 11 |
| 17.08 | 12 |
| 18.11 | 37 |
| 19.43 | 14 |
| 22.27 | 33 |
| 23.07 | 49 |
| 24.33 | 10 |
| 25.50 | 78 |
| 26.54 | 34 |
| 28.62 | 13 |
| 32.09 | 17 |

Form IX has the following XRPD °2θ peaks and relative intensities:

| °2θ | I/Io |
|---|---|
| 5.28 | 47 |
| 8.21 | 10 |
| 12.66 | 52 |
| 13.81 | 19 |
| 15.02 | 20 |
| 16.32 | 58 |
| 17.78 | 73 |
| 18.70 | 42 |
| 19.74 | 85 |
| 22.22 | 100 |
| 23.80 | 29 |
| 24.86 | 12 |
| 26.33 | 37 |
| 28.52 | 26 |
| 29.86 | 16 |
| 31.92 | 12 |
| 33.21 | 19 |
| 34.67 | 16 |
| 38.15 | 25 |
| 39.54 | 11 |

Form X has the following XRPD °2θ peaks and relative intensities:

| °2θ | I/Io |
|---|---|
| 8.75 | 36 |
| 9.67 | 18 |
| 10.56 | 100 |
| 11.28 | 24 |
| 13.51 | 26 |
| 14.82 | 34 |
| 15.80 | 19 |
| 16.04 | 35 |
| 16.32 | 16 |
| 17.61 | 20 |
| 18.07 | 28 |
| 19.26 | 24 |
| 20.30 | 42 |
| 20.78 | 13 |
| 21.33 | 26 |
| 21.98 | 14 |
| 22.87 | 41 |
| 24.00 | 14 |
| 24.28 | 19 |
| 26.06 | 43 |
| 26.44 | 25 |
| 26.78 | 17 |
| 27.45 | 22 |
| 27.80 | 11 |
| 28.06 | 14 |
| 28.26 | 12 |
| 30.86 | 11 |
| 38.11 | 11 | and the amorphous form has a single broad peak from 7.28-30.76 XRPD °2θ.

2. A form of hydrocodone bitartrate which is selected from the group consisting of: Form II, Form III, Form IV, Form V, Form VI, Form VII, Form VIII, Form IX, Form X, and an amorphous form, wherein Form II has XRPD °2θ peaks at 10.39, 17.13, 18.32, 20.86, 21.37, 23.01, 30.24 and 33.55;

Form III has XRPD °2θ peaks at 4.86, 6.74, 8.82, 10.40, 26.76 and 36.40;

Form IV has XRPD °2θ peaks at 7.54, 11.21, 19.21, 22.80 and 25.02;

Form V has XRPD °2θ peaks at 6.57, 12.16, 14.54 and 20.76;

Form VI has XRPD °2θ peaks at 12.54, 12.92, 18.01, 26.15, 28.91, and 32.74;

Form VII has XRPD °2θ peaks at 13.08, 21.64, 21.98 and 28.70;

Form VIII has XRPD °2θ peaks at 7.35, 14.70, 25.50 and 26.54;

Form IX has XRPD °2θ peaks at 8.21, 12.66, 17.78, 19.74, and 22.22;

Form X has XRPD °2θ peaks at 8.75, 10.56, 18.07 and 22.87; and the amorphous form has a single broad peak from 7.28-30.76 XRPD °2θ.

3. A form of claim 1 which is 90-100% pure (wt./wt.).

4. A form of claim 3 that is 95-100% pure.

5. A form of claim 4 that is 98-100% pure.

6. A process to make a Form II of hydrocodone bitartrate of claim 1, which comprises: dissolving hydrocodone bitartrate in a 9:1 (v/v) water:ethanol mix, filtering the solution, and leaving the mixture uncapped to evaporate to dryness to yield Form II.

7. A process to make a Form III of hydrocodone bitartrate of claim 1, which comprises: dissolving hydrocodone bitartrate in water, filtering the solution and adding acetone, cooling to 4 degree C. for 4 days then reducing the temperature to minus 20 degrees C. for 1 day and vacuum filtering the solid formed to yield Form III.

8. A process to make a Form IV of hydrocodone bitartrate of claim 1, which comprises: dissolving hydrocodone bitartrate in water, filtering the solution through a nylon syringe filter, leaving the mixture uncapped to evaporate to dryness, and drying under vacuum to yield Form IV.

9. A process to make a Form V of hydrocodone bitartrate of claim 1, which comprises: dissolving hydrocodone bitartrate in water, filtering the solution through a nylon syringe filter and adding acetone to the filtrate and then placing mixture in a freezer at minus 20 degrees C. for 5 days and recovering solids by vacuum filtration to yield Form V.

10. A process to make a Form VI of hydrocodone bitartrate of claim 1, which comprises: dissolving hydrocodone bitartrate in tetrahydrofuran at 60 degrees C., filtering the solution while warm, cooling to room temperature followed by cooling to 4 degrees C. for 3 days followed by cooling to minus 20 degrees C. for 8 days, collecting the solids by vacuum filtration, and drying under vacuum to yield Form VI.

11. A process to make a Form VII of hydrocodone bitartrate of claim 1, which comprises: dissolving hydrocodone bitartrate in methanol, filtering the solution through a nylon syringe filter, cooling mixture to minus 20 degrees C. for 9 days and removing solids by filtration and then adding ethyl ether to the filtered solution and cooling the resulting mixture to minus 20 degrees C. for 39 days and filtering the solids to yield Form VII.

12. A process to make a Form VIII of hydrocodone bitartrate of claim 1, which comprises: dissolving hydrocodone bitartrate in acetonitrile, filtering the solution through a nylon syringe filter and leaving the mixture loosely capped to evaporate to dryness to yield Form VIII.

13. A process to make a Form IX of hydrocodone bitartrate of claim 1, which comprises: dissolving hydrocodone bitartrate in tetrahydrofuran at 60 degrees C., cooling quickly to the temperature of a dry ice acetone mixture and maintaining at a temperature of minus 20 for 26 days, then removing solids through filtration, and leaving uncovered to evaporate to dryness to yield Form IX.

14. A process to make a Form X of hydrocodone bitartrate of claim 1, which comprises: dissolving hydrocodone bitartrate in acetonitrile, filtering the solution through a nylon syringe filter and leaving the mixture under a foil lid containing 5 pinholes to evaporate to dryness to yield Form X.

15. A process to make a form of hydrocodone bitartrate of claim 1, which comprises: dissolving hydrocodone bitartrate in a 5:1 tetrahydrofuran/water (v/v) mixture, filtering the solution through a nylon syringe filter and leaving the mixture uncapped to evaporate to dryness to yield the amorphous form.

16. A form of hydrocodone bitartrate made by the process of claim 6.

17. A form of hydrocodone bitartrate made by the process of claim 7.

18. A form of hydrocodone bitartrate made by the process of claim 8.

19. A form of hydrocodone bitartrate made by the process of claim 9.

20. A form of hydrocodone bitartrate made by the process of claim 10.

21. A form of hydrocodone bitartrate made by the process of claim 11.

22. A form of hydrocodone bitartrate made by the process of claim 12.

23. A form of hydrocodone bitartrate made by the process of claim13.

24. A form of hydrocodone bitartrate made by the process of claim 14.

25. A form of hydrocodone bitartrate made by the process of claim 15.

26. A composition comprising therapeutically effective amounts of one or more of the Forms of claim 1, optionally in combination with hydrocodone bitartrate, and pharmaceutically acceptable carriers therefor.

27. A method of providing an analgesic effect to a person in need thereof which comprises administering to said person a therapeutic amount of one or more of a Form of claim 1, optionally in combination with hydrocodone bitartrate.

28. A form of claim 2 which is 90-100 % pure (wt./wt.).

29. A form of claim 28 that is 95-100% pure.

30. A form of claim 29 that is 98-100% pure.

* * * * *

UNITED STATES PATENT AND TRADEMARK OFFICE
CERTIFICATE OF CORRECTION

PATENT NO. : 7,625,918 B2  Page 1 of 1
APPLICATION NO. : 11/371377
DATED : December 1, 2009
INVENTOR(S) : Hagen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 504 days.

Signed and Sealed this

Second Day of November, 2010

David J. Kappos
*Director of the United States Patent and Trademark Office*